(12) United States Patent
Claeys et al.

(10) Patent No.: US 8,597,598 B2
(45) Date of Patent: Dec. 3, 2013

(54) SAMPLE PRESENTATION DEVICE FOR RADIATION-BASED ANALYTICAL EQUIPMENT

(71) Applicants: Michael Christian Maximilian Claeys, Sea Point (ZA); Nico Frederik Fischer, Mannheim (DE)

(72) Inventors: Michael Christian Maximilian Claeys, Sea Point (ZA); Nico Frederik Fischer, Mannheim (DE)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 13/659,082

(22) Filed: Oct. 24, 2012

(65) Prior Publication Data

US 2013/0052100 A1     Feb. 28, 2013

Related U.S. Application Data

(63) Continuation-in-part of application No. 13/180,718, filed on Jul. 12, 2011.

(51) Int. Cl.
*B01L 9/06* (2006.01)

(52) U.S. Cl.
USPC ............ 422/562; 422/82.05; 422/82.11; 422/544

(58) Field of Classification Search
USPC ............ 442/82.05, 82.11, 544, 560, 561, 562
See application file for complete search history.

(56) References Cited

U.S. PATENT DOCUMENTS

| 3,254,212 A | 5/1966 | Fanning et al. |
| 6,355,217 B1 | 3/2002 | Kiefersauer et al. |
| 7,909,367 B2 * | 3/2011 | Plant et al. .................... 285/249 |
| 2007/0163799 A1 | 7/2007 | Barnhard et al. |

FOREIGN PATENT DOCUMENTS

| DE | 19842797 | 1/2000 |
| FR | 2856793 | 12/2004 |

OTHER PUBLICATIONS

E. Dedman, International Search Report in PCT/IB2012/053438, Nov. 22, 2012, 6 pages.
Conax Technologies, "Compression Seal Fitting Solutions—The Complete Guide to Pressure and Vacuum Assemblies," Conax Technologies Company Catalogue, vol. 5001C (2007).

(Continued)

*Primary Examiner* — Jill Warden
*Assistant Examiner* — Dwayne K Handy
(74) *Attorney, Agent, or Firm* — Florek & Endres PLLC

(57) ABSTRACT

A sample presentation device for radiation-based analytical equipment comprising a mounting base, a carrier carried by, and adjustable in position, relative to the mounting base, and an arm extending from the carrier and having at its opposite end a terminal member; Each of the carrier and terminal member has a coaxial connector for receiving two opposite end regions of a capillary tube that forms, in use, a reaction cell; A radiant heater, typically an infrared heater, is radially offset from the axis of the coaxial connectors for heating, in use, a capillary tube mounted by way of the coaxial connectors; The carrier and terminal member preferably have heaters associated therewith for heating the flow passages through them; The terminal member preferably has a passage generally coaxial with the connector for receiving a communications conductor carrying a temperature sensor at its end that is operatively located generally centrally within a capillary.

12 Claims, 4 Drawing Sheets

(56) References Cited

OTHER PUBLICATIONS

S.R. Bare et al., "Design and Operation of a High Pressure Reaction Cell for in situ X-ray Absorption Spectroscopy," Catalysis Today, Elsevier, vol. 126, No. 1-2, pp. 18-26 (Jul. 28, 2007).

F.C. Meunier, "The Design and Testing of Kinetically-Appropriate Operando Spectroscopic Cells for Investigating Heterogenous Catalytic Reactions," Chem. Soc. Rev., vol. 39, No. 12, pp. 4602-4614 (Oct. 11, 2010).

S.D.M. Jacques et al., "Recent Progress in the use of in situ X-ray Methods for the Study of Heterogenous Catalysts in Packed-bed Capillary Reactors," Catalysis Today, Elsevier, vol. 145, No. 3-4, pp. 204-212 (Mar. 21, 2009).

E. Dedman, Written Opinion of the International Searching Authority in PCT/IB2012/053438, Nov. 22, 2012, 7 pages.

Machine translation of FR 2856793, Inst Francais Du Petrole (Dec. 31, 2004).

\* cited by examiner

SAMPLE PRESENTATION DEVICE FOR RADIATION-BASED ANALYTICAL EQUIPMENT

The present application is a continuation-in-part of U.S. Ser. No. 13/180,718, filed Jul. 12, 2011, now pending, and claims the benefit of South African Provisional Patent Application No. 2012/04359, filed Jun. 14, 2012.

FIELD OF THE INVENTION

This invention relates to a sample presentation device for radiation-based analytical equipment and, more particularly, radiation-based analytical laboratory equipment such as X-ray diffraction as well as synchrotron and neutron based equipment.

Still more particularly, the invention relates to a sample presentation device for use in association with equipment such as laboratory equipment that permits the flow of fluids, especially but not necessarily gases, over or through a sample being examined, typically at elevated temperature and pressure. The sample being examined may be any crystalline material, for example a heterogeneous catalyst for the purpose of carrying out a suitable catalytic reaction.

BACKGROUND TO THE INVENTION

Current trends in heterogeneous catalysis research as well as in material sciences and related sciences have led to an increased drive to apply known characterisation techniques, such as powder X-ray diffraction, under elevated temperatures, pressures and changing gas and/or liquid atmospheres. Commercially available in-situ X-ray diffraction chambers (for example those produced by the Austrian company Anton-Paar) do facilitate the study of materials at elevated temperatures (up to 900° C.), pressures (up to 10 bar) and under different gas atmospheres.

However, their design entails a fairly large volume reaction chamber (approx. 500 ml) into which the sample is inserted on a plate-like sample holder. The most well known example known to applicant in their range is a model known as XRK. A large volume reaction chamber of this nature does not allow for a rapid changeover of gasses fed to the reaction chamber. As a result, an appreciable period of time elapses when the gas composition in the feed is changed before the reaction to the change can be studied. Secondly, those reaction chambers are provided with beryllium (category 1 carcinogen) or similar X-ray invisible windows that limit the temperatures and pressures that can be applied to the reaction chamber. Thirdly, they are unable to accommodate liquid products and/or corrosive or oxidising gasses and vapours such as water either in the feed or in the reaction products stream such as would occur in a fixed bed reactor system. These cells are thus generally limited to dry conditions that do not result in corrosion.

The bulky design of the reactor chamber and the plate-like sample holder further does not allow a realistic plug flow like flow pattern through the powder sample due to the presence of dead volumes and poorly defined concentration gradients. This does not allow the determination of kinetic information in, for example catalyst testing, and always leaves a doubt whether the chosen conditions do actually represent the conditions in real live applications.

A sample presentation device using a glass capillary as the reaction chamber has been proposed in French patent number FR2856793 that, as far as applicant is aware, has not yet been made commercially available. The capillary has an electrical heating element carried in a sleeve that substantially surrounds the capillary tube and a thermocouple associated with that sleeve is employed to measure the temperature of the sleeve from which the temperature within the capillary reaction chamber is inferred. The temperature range is stated to be up to 250° C. with a pressure range up to 5 bars. An important feature of the device described is that the reaction chamber can be oscillated about its own axis in order to better present the sample within the capillary reaction chamber to the X-radiation. As far as applicant is concerned the device described does not fulfill requirements and also has shortcomings in its range of operation. No particular mention is made of liquids or vapours in the feed or product streams.

Synchrotron based applications rely on capillaries much more as reaction vessels and plug flow reactors for studies in catalysis, biology and material sciences. However the small number of synchrotron facilities available worldwide and their enormity in size and cost render the use of a synchrotron out of the reach of, and generally unavailable to, the majority of researchers and small-scale facilities. Laboratory powder X-ray diffractometers are, on the other hand, wide spread and are commonly available and frequently used in modern research and other facilities. It is also noted that, as far as the applicant is aware, synchrotrons typically employ a hot air gun to effect heating of the sample which is a technique that is unsuitable for laboratory equipment.

Applicant believes that there is a need to provide a sample presentation device for radiation-based analytical equipment that is simple, cost effective, and yet has practical operating ranges.

Applicant also believes that there is a need to provide a sample presentation device for radiation-based analytical equipment that is able to accommodate liquids and vapours in the feed and product streams.

SUMMARY OF THE INVENTION

In accordance with this invention there is provided a sample presentation device for radiation-based analytical equipment comprising a mounting base, a carrier carried by, and adjustable in position relative to, the mounting base, and an arm extending from the carrier and having at its opposite end a terminal member and wherein the carrier and terminal member each have coaxial connectors for receiving two opposite end regions of a capillary tube that forms, in use, a reaction cell, and at least one radiant heater radially offset from the axis of the coaxial connectors for heating, in use, a capillary tube mounted by way of the coaxial connectors.

Further features of the invention provide for the radiant heater to be an infrared heater; for the radiant heater to be carried by the arm in a position radially opposite a region to be occupied by the central region of a capillary tube in use; for a generally channel shaped reflective shield to be provided for directing radiation from the radiant heater towards a position to be occupied by a capillary tube, in use; for the carrier and terminal member to have flow paths passing therethrough and communicating with the coaxial connectors and wherein the flow paths are associated with heating means whereby they can be heated, in use; for the carrier and terminal member to each be made of a solid block of thermally conductive material in which instance they are preferably configured for receiving a removable heater insert, typically in a blind hole; for the end of each flow path remote from its associated connector to have an axis extending at right angles to that of the connector; and for the terminal member to have a passage generally coaxial with the connector for receiving a communications conductor carrying a temperature sensor, typically a thermocouple, at its end that is operatively located generally centrally within a capillary tube but outside of any beam path.

Still further features of the invention provide for the mounting base to be a metal plate shaped and configured for mounting on a particular item of radiation-based analytical equipment; for the carrier to be attached to the mounting base by way of a slide and guide arrangement that may be of a inwardly lipped channel configuration allowing adjustable positioning of the carrier on the mounting base along at least one axis that is typically a vertical axis in use, but may in the alternative be a horizontal axis; for the arm to be adjustable in position in the direction of its own length relative to either the carrier or the terminal member to facilitate installation and removal of a capillary tube between the connectors; and for the length of the arm to extend at generally right angles to the direction of adjustment of the carrier on the mounting base.

One form of connector that is particularly preferred is a compression fitting for forming an effective seal between a body part and an outer surface of a capillary tube wherein the compression fitting comprises a body having a passage therein, a cavity coaxial with the passage for accommodating a seal, a generally cylindrical seal accommodated within the cavity wherein the seal is made of a suitably deformable but incompressible material and has a bore passing axially through the seal for accommodating a capillary tube in use, a follower movable into and out of the cavity in order to compress the seal in the axial direction, and a screw threaded cap for urging the follower into the cavity, wherein the follower and body have cooperating formations associated therewith whereby rotation of the follower relative to the body is prevented and movement of the follower relative to the body is permitted in an axial direction only.

Such cooperating formations may include a pin or key having its length extending parallel to the axis of the body and laterally offset therefrom with the pin or key cooperating with a hole or groove in the body and a corresponding hole or notch in a flange extending radially outwards from the periphery of the follower. The outer diameter of the seal is preferably equal to at least three times the diameter of the bore through it and generally from four to six times the diameter of the bore through it. The seal may be made of a suitably temperature resistant material, especially a suitable silicon rubber material.

The term capillary as used in this specification is intended to include all appropriate and suitable diameters of tubes that are typically made of specialist glass such as borosilicate glass and quartz glass; specialist polymer material; or grown sapphire; in each instance selected to be suitably transparent to radiation, especially X-radiation. Of course the diameter of the capillary will be limited by the elevated pressures to be used and, in addition, the wall thickness of the capillary tube should be such that radiation losses are minimized. Typically the diameter will be within the range of 0.2 to 2 mm with a commonly used size being of the order of 1 mm with a wall thickness of about 0.01 mm.

It is envisaged that a sample presentation device according to the invention should be capable of operating at temperatures of up to 500° C. and more and at pressures of up to 10 bars and more. It is also possible to use the sample presentation device in instances in which feed and product streams from, for example, a catalyst sample, can include liquids or vapours in which instance the carrier and terminal member can be heated appropriately, for example to temperatures of between 200° C. and 300° C. in the instance of an X-ray diffraction analysis of a Fischer-Tropsch reaction utilizing an alumina-supported cobalt catalyst.

It is to be mentioned that it is considered that the invention is particularly well-suited for application in X-ray diffraction equipment that operates on a reflection basis rather than on the transmission basis as in the instance of a synchrotron. The invention may also be advantageously applicable in extended X-ray absorption fine structure [EXAFS] and X-ray absorption near edge structure [XANES] analyses.

The above and other features of the invention will become more apparent from the following description of one embodiment thereof with reference to the accompanying drawings.

DETAILED DESCRIPTION WITH REFERENCE TO THE DRAWINGS

Figure 1:
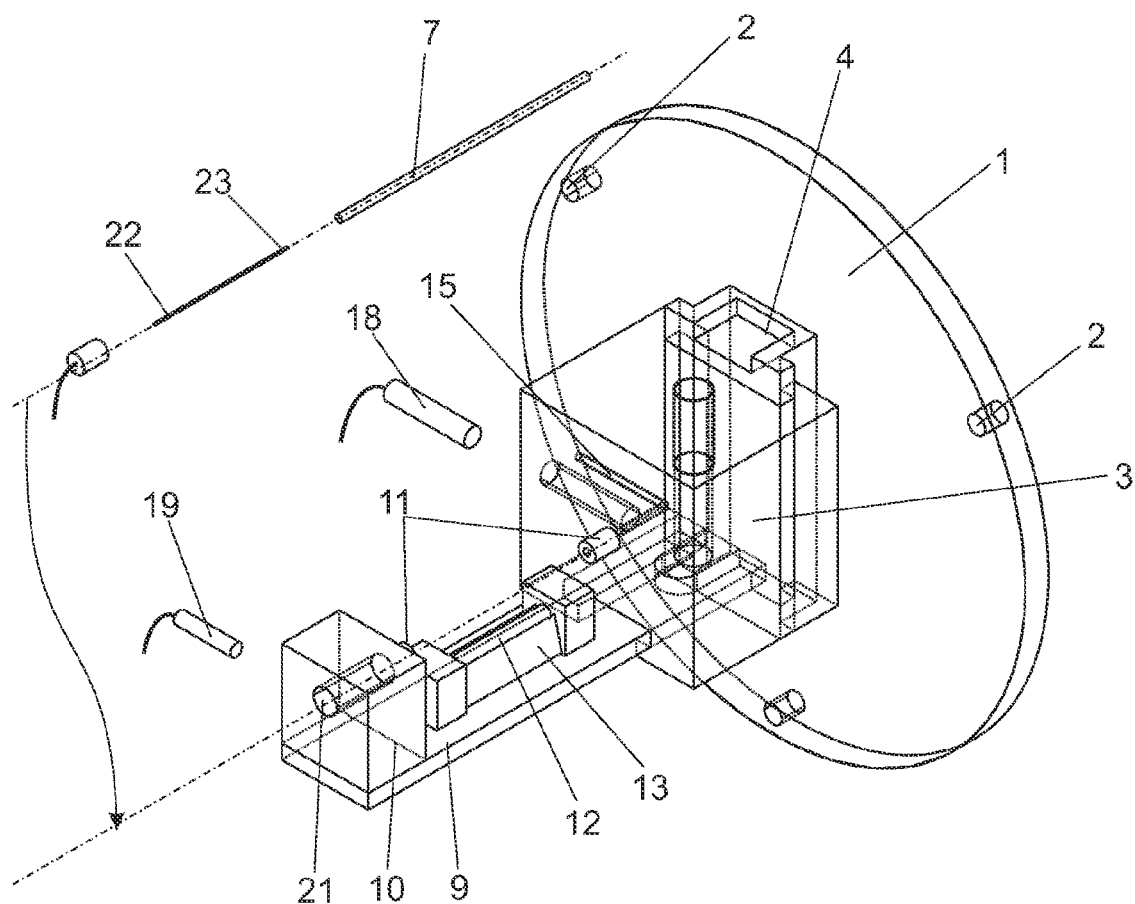
FIG. 1 is an isometric view of one embodiment of sample presentation device according to the invention with detail omitted for purposes of clarity.

In the embodiment of the invention illustrated in the drawings, a sample presentation device that is particularly designed for use on analytical X-ray diffraction equipment comprises a mounting base in the form of a metal plate (1) shaped and configured for mounting on a particular item of radiation-based analytical equipment, in this instance in the form of a Bruker D8 X-Ray Diffractometer that operates on the basis of reflected radiation. The metal plate has holes (2) for securing it to the laboratory equipment, and typically to the goniometer of the diffractometer, generally in an operatively vertical plane.

The mounting plate supports a carrier (3) in the form of a solid block of thermally conductive material, typically stainless steel, attached to the mounting base by way of, in this instance, a vertically orientated slide and guide arrangement (4) that is of an inwardly lipped channel configuration. A thumbwheel (5) and associated screw threaded components (not illustrated) allows the vertical position of the carrier to be adjusted relative to the mounting plate in order to align a sample holder in the form of a capillary tube (7) with the zone of radiation, in use.

The capillary tube in this embodiment of the invention is made of borosilicate glass and has an outer diameter of 1 mm and an inner diameter of 0.98 mm. Typically, the length of a capillary tube will be about 75 mm but different lengths can be used according to requirements. It is to be noted that the pressure rating of the capillaries is higher than that of commercially available large in-situ cells.

A generally horizontal arm (9) extends from the carrier at right angles to the direction of adjustment of the carrier on the mounting plate and such arm has at its opposite end a terminal member (10) also in the form of a solid stainless steel block.

The carrier and terminal member each have coaxial connectors (11) for receiving the two opposite end regions of a capillary tube (7) that forms a reaction cell. The connectors are conveniently of the compression seal type and may employ a graphite ferrule or an elastic o-ring for compressive sealing onto the outer surface of the capillary tube in appropriate instances. However, the connectors are preferably in the form of compression seals of the type that is more fully described below with reference to FIGS. 4 and 5 or FIG. 6 of the accompanying drawings. Such compression seals are especially suitable in the instance of fragile or deformable capillary tubes.

Reverting to the general construction, the arm is adjustable in the direction of its own length relative to the carrier so that the spacing between the carrier and terminal member can be selected according to the length of the particular capillary tube that is in use. This also enables the terminal member to be moved outwards in order to facilitate the introduction or removal of a capillary tube relative to the connectors.

Mounted on the arm is a radiant infrared heater (12) that is radially offset from an installed capillary tube for heating it and a sample contained therein. In order to achieve optimum usage of the heat given off by the infrared heater, a generally channel shaped reflective shield (13) may be provided for reflecting radiation from the radiant heater towards a position occupied by a capillary tube, in use.

Figure 2:
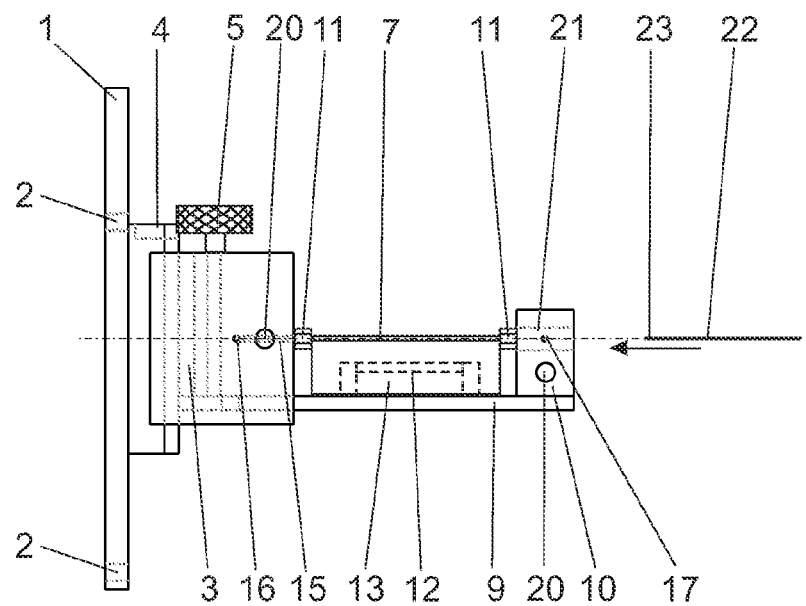
FIG. 2 is a side view thereof.
Figure 3:
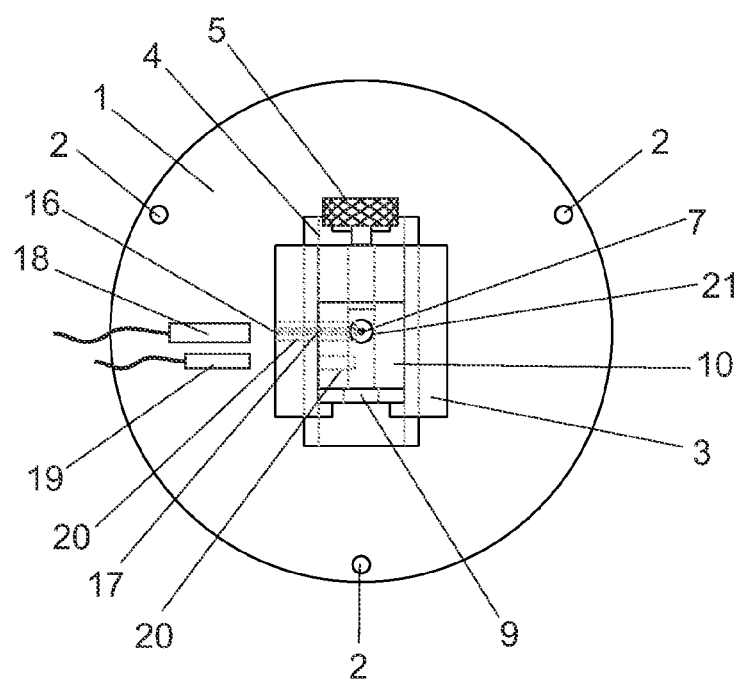
FIG. 3 is a front view thereof.

The carrier (3) and terminal member (10) each have flow paths (15) passing therethrough and communicating with the associated coaxial connector. The end (16, 17) of each flow path remote from its associated connector (see FIG. 2) has the axis of its inlet/outlet extending at right angles to the axes of the connectors.

The flow paths are arranged to be heated by removable heating inserts (18, 19) that are of right circular cylindrical shape so as to be received in a blind hole (20) in the carrier or terminal member. This arrangement ensures that the entire block, in each instance, may be heated, as and when required. The arrangement is such that the carrier and terminal member may be heated to temperatures which are high enough to avoid condensation of vapours in the feed or the reaction products.

Figure 4:
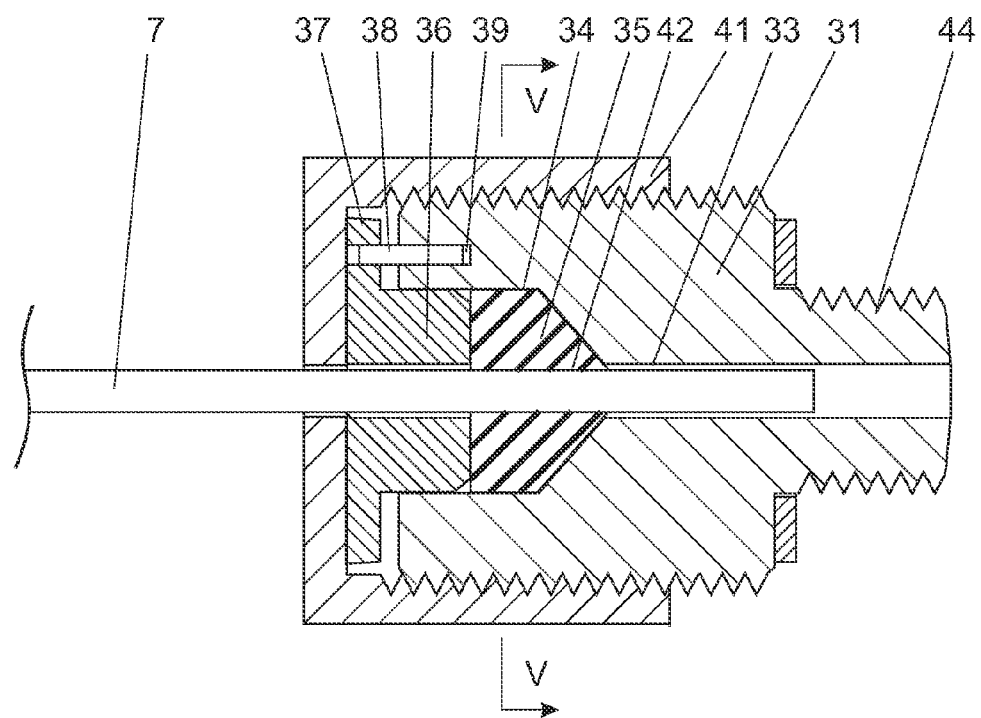
FIG. 4 is an enlarged sectional elevation of one preferred form of connector in the form of a compression fitting.
Figure 5:
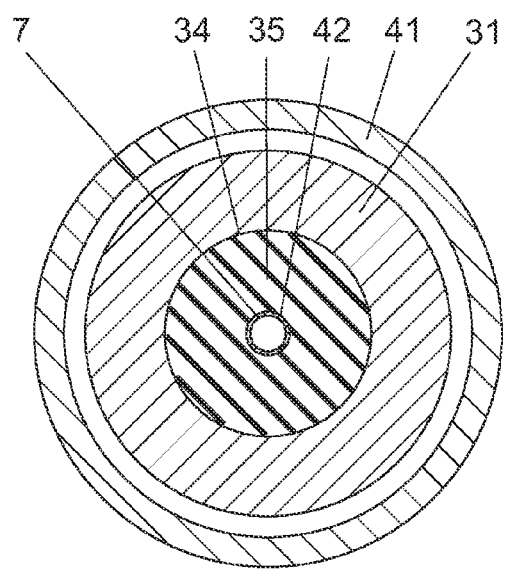
FIG. 5 is a cross-section thereof taken a long line V-V in FIG. 4.

In the instance of the terminal member a passage (21) is provided coaxially with the connector for receiving a communications conductor (22) carrying a thermocouple (23) at its end that is operatively located generally centrally within a capillary tube. Turning now to the compression seal that is illustrated in FIGS. 4 and 5 of the drawings, a compression fitting is provided that is particularly adapted to form an effective seal between a body part (31) and an outer surface of the thin walled glass capillary tube (7). A passage (33) in the body opens into a cavity (34) that is coaxial with the passage.

The cavity is of generally right circular cylindrical shape with its inner end being formed into a truncated conical shape. The cavity accommodates a seal (35) that is of generally complementary shape so as to conform to the shape of the cavity whilst leaving an unoccupied end region that receives a generally cylindrical follower (36) that is movable into the cavity in order to apply an axially directed compressive force to the seal.

The follower has at its outer end a radially extending flange (37) that has a hole through it and through which a formation in the form of a pin (38) passes. The pin extends out of a blind hole (39) in the body with its axis parallel to the axis of the body but laterally offset therefrom.

A coaxial union nut in the form of a cap (41) is internally screw threaded to cooperate with an external screw thread on the body so that the cap can be screwed onto the body to urge the follower into the cavity in order to compress the seal axially in the well-known manner of a compression seal. The presence of the pin and cooperating hole through the flange of the follower ensure that movement of the follower is strictly axial and that no twisting force is transmitted to the tube.

The seal has a bore (42) passing axially through it with the dimensions of the bore of being appropriate to the outer diameter of the capillary tube (7) with which the fitting is to be used. As a general rule therefore different seals will be provided for different diameter capillary tubes. The outer diameter of the seal is, in this instance, equal to at least five times the diameter of the bore through it. This type of dimension ensures that there is an adequate body of the material from which the seal is made to distribute the sealing force substantially evenly over the outer surface of the capillary tube. In this particular instance the bore through the seal is dimensioned to accommodate a capillary tube having an outer diameter of about 1 mm.

The seal is made of a suitably deformable but incompressible material and in this particular instance, it is made of a suitable silicon rubber that exhibits good properties at somewhat elevated temperatures and pressures.

The body has a screw threaded spigot (44) extending from the end thereof opposite the cap and the screw threaded spigot can be used to attach the fitting to a cooperating socket in the carrier (3) and terminal member (10) respectively.

With a capillary tube in position in the fitting, the cap can simply be tightened by using finger force only in order to achieve a highly effective seal on the outer surface of a capillary tube. Such a seal may be capable of withstanding an internal pressure of about 10 bars, or more.

Figure 6:
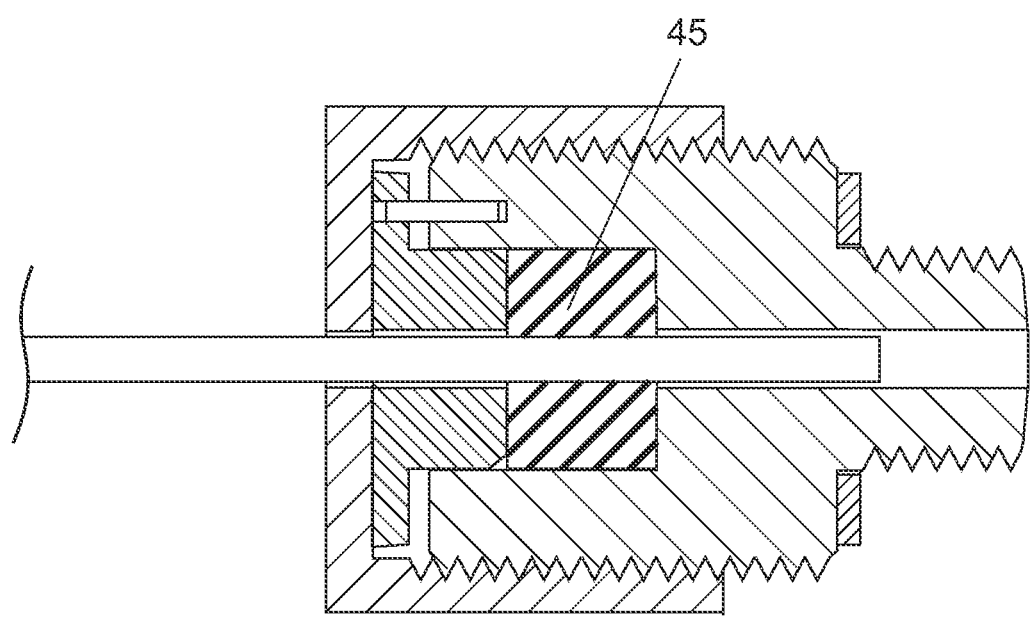
FIG. 6 is a view similar to FIG. 4 showing a slight variation thereof.

The shape of the seal can be varied widely and a simple right circular cylindrical shape, as indicated by numeral (15) in FIG. 6, is also expected to operate effectively.

It is to be noted that a compression seal of this nature has also been successfully applied to capillary tubes made of a temperature resistant polymer that allows for very high X-ray flux with almost no intensity losses such as a polymer sold under the name KAPTON, by the international company DUPONT. Such a material may not be fragile, but may be somewhat deformable and require internal support using an internal support tube (e.g. made from stainless steel) which has an outer diameter roughly matching the inner diameter of the polymer capillary tube. Such an internal support tube would be placed just under the seal.

A sample presentation device as described above is capable of operating at temperatures of up to and possibly exceeding 500° C. and pressures of up to and possibly exceeding 10 bars.

In use, a permeable plug is installed at one end region of a capillary tube that is then filled with the sample to be tested, possibly a catalyst. Whilst filling the capillary tube, the thermocouple may be positioned generally centrally within the tube. The thermocouple would not normally be in the middle of the capillary but a short distance away so as to be outside of the beam path, i.e. about 1 cm or so away from the centre. It must be ensured that the thermocouple is not "seen" by the radiation. The end from which filling took place is then closed with another permeable plug.

Although preferable for accurate control, it is not an absolute necessity to have the thermocouple inside the capillary. It can also be outside, but located as close as possible to the reactor (again outside of the beam path). This allows the use of thermocouples with larger diameters to be employed.

The capillary tube is then located in the device and the connectors are tightened in order to seal onto the outer surface of the capillary tube. The communications conductor (22) carrying the thermocouple will then extend through the passage (21) in the terminal member. Any additional sealing can be achieved in any suitable manner such as by the use of Teflon tape and O-rings.

Vertical alignment of the capillary tube can then be effected using the thumbwheel (5) in order to achieve the ideal/correct position for reflection X-ray diffraction. The relevant position required varies depending on the diameter of the capillary.

In use, consequent on the small volume and geometry of the capillary reaction chamber, no dead volumes form and a near ideal plug flow behaviour can generally be expected. This allows a quick change over of gases/atmospheres, e.g. from reactive to inert to interrupt reactions or to study the effect of different gas compositions. The well defined flow pattern also allows sampling of the exhaust gas stream and analysis to be carried out on activity, selectivity and even kinetic data in reaction studies. A separate experiment in a specifically designed laboratory scale fixed bed reactor to obtain such results becomes redundant as reaction data are collected simultaneously with the X-ray diffraction measurements.

It is to be noted that the materials used in the embodiment of the invention described above are inert to at least most possible feed streams and reaction products. There are also no limitations in conversion to avoid condensation of heavier reaction products. The materials used obviate problems associated with the oxidation of the beryllium windows which would lead to decreased X-ray diffraction visibility. The use of borosilicate glass capillaries provides a minimal contribution of the capillary material to the X-ray diffraction spectrum. The usage of non corroding materials allows the feeding/formation of liquids and vapours without the danger of damaging the cell.

It is envisaged that use of a sample presentation device according to the invention will facilitate novel insights into phase and crystallite size changes of various materials at relevant operating conditions in very controlled environments. Due to its ability to provide reaction data (activity, selectivity, yields, etc.) the sample presentation device according to the invention also decreases the turn-over time in materials screening while supplying a more concise view on the studied system. Small sample volumes also reduce the cost of sample testing. Near ideal plug flow behaviour and lack of dead volumes also allows the collection of kinetic data in parallel with the X-ray diffraction studies, further saving time and money.

Direct temperature control with the thermocouple in the centre of the capillary increases accuracy and utility of the data obtained. Heating with infra red heaters as opposed to hot air guns as is normally done in synchrotron facilities increases the safety of the operation due to the localized power output of the infra red heaters.

The capillary tube presentation cell can be attached to every commercial X-ray diffactometer by simply adjusting or replacing the backing plate. No other adjustments to the design need to be made.

The invention therefore facilitates the application of capillaries as plug flow reactors in radiation-based analytical laboratory equipment such as commercial laboratory powder X-ray diffractometers.

The invention can, however, also be used at synchrotron facilities and make the lives of the users of such a facility easier too.

Numerous variations may be made to the embodiment of the invention described above without departing from the scope hereof. In particular, a possible extension of the device described is the option to move the capillary tube (or the whole cell) along the capillary axis. This would enable studies of local changes of material along this axis to be conducted, e.g. as a consequence of changes of concentration of educts and products along this axis during reaction work.

Further extensions of the concept may include advanced external control of the cell, including motorised capillary adjustment and system integrated temperature control fully synchronised with X-ray diffraction scans. A motorised oscillation by say +/−90° of the capillary may be introduced as an added option in order to minimise effects of 'preferred crystal orientation'.

It is also possible to position the carrier horizontally as an alternative to the orientation described above. This would enable a study of compositional gradients of the material along this axis which may occur in catalytic reactions with high degrees of conversion of the feed material, that is to say, with severe concentration profiles.

The invention claimed is:

1. A sample presentation device for radiation-based analytical equipment comprising a mounting base in the form of a metal plate shaped and configured for mounting on a particular item of radiation-based analytical equipment, a carrier carried by, and adjustable in position relative to, the mounting base, and an arm extending from the carrier and having at its opposite end a terminal member and wherein the carrier and terminal member each have coaxial connectors for receiving two opposite end regions of a capillary tube that forms, in use, a reaction cell, and at least one radiant heater radially offset from the axis of the coaxial connectors for heating, in use, a capillary tube mounted by way of the coaxial connectors wherein the radiant heater is carried by the arm in a position radially opposite a region to be occupied by the central region of a capillary tube in use and wherein the carrier and terminal member each have a flow path passing therethrough and communicating with the coaxial connectors and a separate heater is associated with each of the flow paths whereby they can be heated, in use.

2. A sample presentation device as claimed in claim 1 in which the radiant heater is an infrared heater.

3. A sample presentation device as claimed in claim 1 in which a generally channel shaped reflective shield is provided for directing radiation from the radiant heater towards a position to be occupied by a capillary tube, in use.

4. A sample presentation device as claimed in claim 1 in which the carrier and terminal member are each made of a solid block of thermally conductive material in which instance a passage is provided in each of them receiving an optionally removable separate heater insert.

5. A sample presentation device as claimed in claim 1 in which an end of each flow path remote from its associated connector has an axis extending at right angles to that of the connector.

6. A sample presentation device as claimed in claim 1 in which the terminal member has a passage generally coaxial with the connector for receiving a communications conductor carrying a temperature sensor at its end that is operatively located generally centrally within a capillary but outside of any beam path.

7. A sample presentation device as claimed in claim 1 in which the carrier is attached to the mounting base by way of a slide and guide arrangement of an inwardly lipped channel configuration allowing adjustable positioning of the carrier on the mounting base along at least one axis in use.

8. A sample presentation device as claimed in claim 1 in which the length of the arm extends at generally right angles to the direction of adjustment of the carrier on the mounting base.

9. A sample presentation device as claimed in claim 1 in which each connector is a compression fitting for forming an effective seal between a body part and an outer surface of a capillary tube wherein the compression fitting comprises a body having a passage therein, a cavity coaxial with the passage for accommodating a seal, a generally cylindrical seal accommodated within the cavity wherein the seal is made of a suitably deformable but incompressible material and has a bore passing axially through the seal for accommodating a capillary tube in use, a follower movable into and out of the cavity in order to compress the seal in the axial direction, and a screw threaded cap for urging the follower into the cavity, wherein the follower and body have cooperating formations associated therewith whereby rotation of the follower relative to the body is prevented and movement of the follower relative to the body is permitted in an axial direction only.

10. A sample presentation device as claimed in claim 9 in which the cooperating formations include a pin or key having its length extending parallel to the axis of the body and laterally offset therefrom with the pin or key cooperating with a hole or groove in the body and a corresponding hole or notch in a flange extending radially outwards from the periphery of the follower.

11. A sample presentation device as claimed in claim 9 in which the outer diameter of the seal is equal to at least three times the diameter of the bore through it.

12. A sample presentation device as claimed in claim 9 in which the seal is made of a suitable silicon rubber material.

\* \* \* \* \*